United States Patent [19]

Wardlaw

[11] 4,258,713
[45] Mar. 31, 1981

[54] AUTOMATIC DISPOSABLE HYPODERMIC SYRINGE

[76] Inventor: Stephen C. Wardlaw, 128 Sunset Hill Dr., Branford, Conn. 06405

[21] Appl. No.: 59,903

[22] Filed: Jul. 23, 1979

[51] Int. Cl.³ .............................................. A61M 5/00
[52] U.S. Cl. .......................... 128/218 F; 128/218 DA
[58] Field of Search ....... 128/218 F, 218 D, 218 DA, 128/215, 216

[56] References Cited

U.S. PATENT DOCUMENTS

| | | | |
|---|---|---|---|
| 3,066,670 | 12/1962 | Stauffer | 128/218 F |
| 3,136,313 | 6/1964 | Enstrom et al. | 128/218 F |
| 3,605,744 | 9/1971 | Dwyer | 128/218 F |
| 3,702,609 | 11/1972 | Steiner | 128/218 F |
| 3,941,130 | 3/1976 | Tibbs | 128/218 F |

*Primary Examiner*—John D. Yasko
*Attorney, Agent, or Firm*—William W. Jones

[57] ABSTRACT

An improved automatic disposable hypodermic syringe having a retracted needle which is driven by a spring to administer an injection. The needle is contained in a housing and is driven from the housing to administer the injection. An external release mechanism is provided so that the syringe can be operated by an untrained person, if necessary. The needle is held in place in the housing in its retracted position by being embedded in a mass of crushable material which is compressed when the device is actuated to allow the needle to be driven to the extended injecting position.

8 Claims, 6 Drawing Figures

AUTOMATIC DISPOSABLE HYPODERMIC SYRINGE

This invention is related to the inventions disclosed in my co-pending applications Ser. Nos. 955,773, filed Oct. 30, 1978; 955,774, filed Oct. 30, 1978; 972,756, filed Dec. 26, 1978; and 21,483, filed Mar. 19, 1979.

This invention and the above-noted prior applications relate to improvements in automatic hypodermic syringes for use in administering medications and the like. It has been established that there exists a definite need for a pre-loaded automatically operable hypodermic syringe which can be used by trained and untrained personnel alike. This type of automatic syringe can be used to inject such medications as insulin, adrenalin, heparin, atropine, and the like. By using a pre-loaded automatic syringe, problems relating to proper dosage and manually inserting the needle into the recipient's skin are avoided. The automatic syringe can be made sterile and can be easily stored or even carried about on the person of the user with no problems.

In order to compete with conventional syringes in the market place, the automatic syringe must be made as inexpensively as possible. There are many automatic syringe designs described in the prior art, however, the vast majority of the truly automatic types of these syringes are of complicated construction and, therefore, not particularly suited for mass production, assembly, and use due to high cost of manufacturing and filling.

Another necessary feature of an automatic hypodermic syringe suited for mass usage, particularly by untrained personnel, is that the syringe be constructed so as to safeguard against accidental actuation. Thus, an automatic syringe should include a safety lock whereby it cannot be discharged accidentally, and the safety feature should be of simple, inexpensive construction.

The embodiments of the automatic hypodermic syringe of this invention are of simple construction and design, are quickly and easily assembled, and include a simple yet effective release and cooperating safety device which simplifies operation but minimizes the likelihood of accidental discharge.

It is, therefore, an object of this invention to provide an automatic hypodermic syringe for general use in administering medications which syringe may be inexpensively manufactured.

It is an additional object of this invention to provide a syringe of the character described which includes an inexpensive, simple to operate integral release mechanism.

It is a further object of this invention to provide a syringe of the character described which includes a simple yet reliable safety mechanism for minimizing the likelihood of accidental discharge.

It is yet another object of this invention to provide a syringe of the character described which can be quickly and easily assembled in final form after being loaded with the medication to be dispensed.

These and other objects and advantages of the syringe of this invention will become more readily apparent from the following detailed description of several preferred embodiments thereof taken in conjunction with the accompanying drawings, in which.

Figure 5:
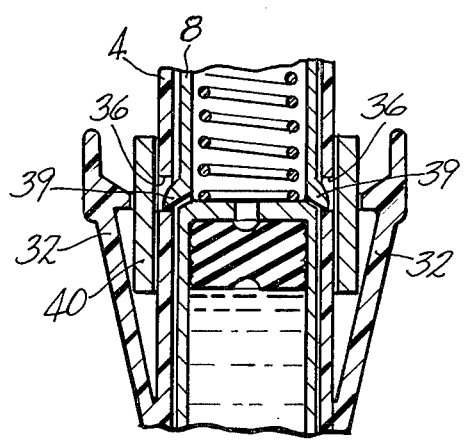
Figure 6:
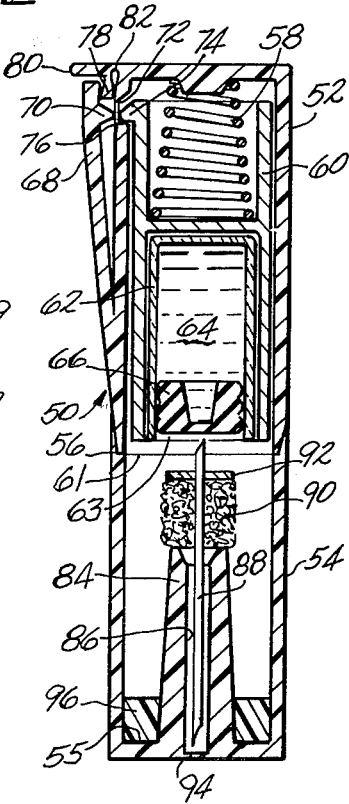

FIG. 5 is an axial sectional view of a portion of still another embodiment of the syringe of this invention showing a double release system in conjunction with a safety device which further lessens the likelihood of accidental actuation of the device; and FIG. 6 is an axial sectional view of an additional embodiment of the syringe of this invention having a basic two-piece housing and showing a modified safety device for lessening the likelihood of accidental discharge.

Figure 1:
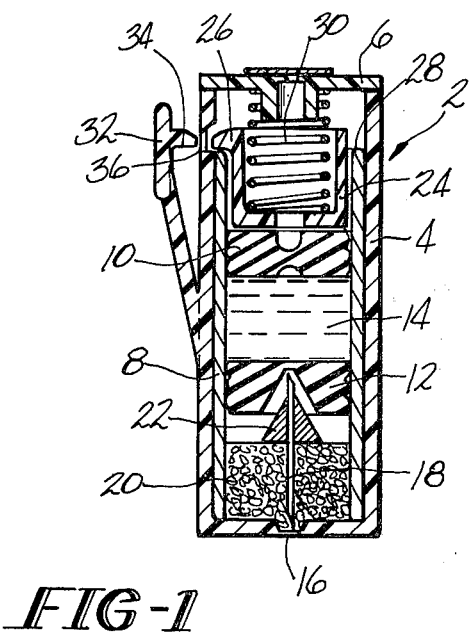
FIG. 1 is an axial sectional view of one embodiment of a syringe formed in accordance with this invention showing a novel needle-holding means, and a simple, inexpensive actuating mechanism, the syringe being shown in the cocked position.

Referring now to the drawings, there is shown in FIG. 1 an automatic hypodermic syringe which is disposable after a single use, the syringe being denoted generally by the numeral 2. The device includes a cup-shaped housing 4 of injection molded plastic closed by a cap 6 which is adhesively secured to the housing 4. Within the housing 4, there is disposed an annular glass or medication-compatible plastic liner 8 in which are slidably disposed upper and lower plunger members 10 and 12, respectively, made from an elastomeric material such as butyl rubber, which is compatible with the medication contained in the syringe. The medication dose 14 is disposed between the plunger members 10 and 12, within the liner 8.

On the lower face of the housing 4, there is formed a thin-walled portion 16 which is pierced by the needle 18 when the device is actuated to deliver a dose of medication. The needle 18 is embedded in a column of crushable foam material 20 such as open-cell polyurethane or open-cell polyethylene, or the like. The column 20 serves to properly position the needle 18 in the housing 4, properly spaced from the thin-walled portion 16, and from the lower plunger member 12. A ferrule 22 of metal or hard plastic is secured to the needle 18 adjacent to an end surface of the foam column 20 to provide a bearing surface which compresses the foam column 20 when the needle is driven through the thin-walled portion 16 of the housing 4. The ferrule 22 also serves as a driving member which acts to drive the needle 18 through the thin-walled portion 16 of the housing when contacted by the lower plunger member 12 as the latter is driven downwardly through the liner 8.

Disposed above the upper plunger member 10 is a cup-shaped spring retainer-catch member 24. The member 24 is formed with an inwardly deflectable catch finger 26 which is biased against the upper end wall 28 of the liner 8 by means of a compressed coil spring 30. A release arm 32 is formed as an integral part of the housing 4 and is inwardly pressed to move an actuating projection 34 through an aligned opening 36 in the housing 4 and against the catch finger 26 to disengage the latter from the liner end wall 28. Thereupon, the spring 30 drives the catch member 24 and upper plunger member 10 downwardly. When acted upon by the upper plunger member 10, the liquid medication dose 14 pushes the lower plunger member 12 downwardly through the liner 8 and against the needle and ferrule 22. It will be noted that both ends of the needle 18 are sharpened to a point. The lower plunger member 12 is then pierced by the needle 18 while engagement between the moving plunger member 12 and ferrule 22 drives the needle 18 through the thin-walled portion 16 of the housing 4, crushing the foam column 20, and driving the needle 18 into the flesh of the user. The upper plunger member 10 then continues through the liner 8 pumping the medication 14 through the needle 18 and into the user. After a single use, the device is discarded. The device can be contained in a sterile wrapper (not shown) prior to use, or tape strips can be used to seal any openings in the housing after sterilization of the interior of the device.

Figure 2:
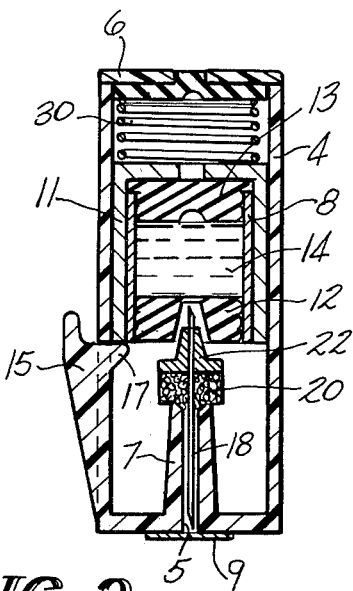
FIG. 2 is an axial sectional view of a second embodiment of the syringe of this invention showing a modified needle holder and a different, yet inexpensive, actuation mechanism.

Referring now to FIG. 2, there is shown a modified hypodermic syringe which includes a housing member 4 having a top closure cap 6 adhesively secured thereto. A needle passage 5 extends through an upwardly projecting pedestal 7 and opens through the bottom wall of the housing 4. A tape strip 9 closes the needle passage 5 to maintain internal sterility of the device. Alternatively, a thinned portion of the end wall could be used to seal the entrance as in FIG. 1. A compressed coil spring 36 biases a cup-shaped holder 11 downwardly within the housing 4. Within the cup-shaped holder 11, there is disposed a glass or plastic medication-compatible liner 8. The upper end of the liner 8 is closed by an elastomeric plug 13, and the lower end is closed by an elastomeric plunger 12. Within the liner 8 and between the plug 13 and plunger 12, there is disposed the liquid medication dose 14 to be administered. Disposed within the needle passage 5 is a double-pointed needle 18. The needle 18 is properly positioned by means of a column 20 of crushable foam material in which the needle 18 is embedded, and which is positioned on the pedestal 7. A metal or hard plastic ferrule 22 is secured to the needle 18 between the foam column 20 and the plunger 12. A catch member 15 is formed as an integral part of the housing 4, the catch member 15 including a portion 17 which projects into the housing 4 to engage the lower end of the cup-shaped member 11 to hold the cup-shaped member 11 and the components carried thereby in a ready-to-use position wherein the spring 36 is compressed and ready to operate the syringe. The catch member 15 is preferably surrounded by a thin web of plastic material integral with the remainder of the housing member 4. To operate the syringe, the catch member 15 is first pressed into the housing member 4 to fracture the surrounding thin web, and then pulled radially outwardly to withdraw the portion 17 from the housing member 4, thereby releasing the cup-shaped member 11 and associated components permitting the same to be driven by the spring 36. Operation of the syringe is similar to that previously described in that the plunger 12 is driven against the needle 18 and ferrule 22 causing perforation of the plunger 12 by the needle 18. Continued movement of the plunger 12 and needle 18-ferrule 22 causes the foam column 20 to be crushed on the pedestal 7 thereby causing the needle 18 to pierce the tape 9 and be driven into the patient's skin. Once the ferrule 22 is driven against the pedestal 7, movement of the needle 18 stops and the plunger 12 is driven upwardly into the liner 8 causing the medication 14 to be forced out of the liner 8, through the needle 18 and into the patient.

Figure 3:
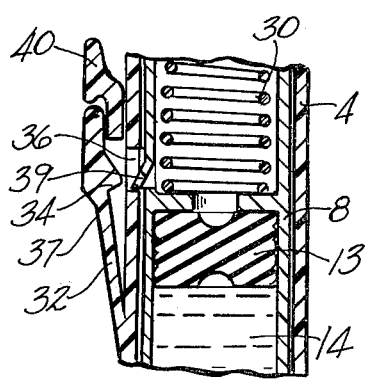
FIG. 3 is an axial sectional view of a portion of yet another embodiment of the syringe of this invention showing an actuating mechanism similar to that shown in FIG. 1 with a safety device for lessening the likelihood of accidental actuation of the syringe.
Figure 4:
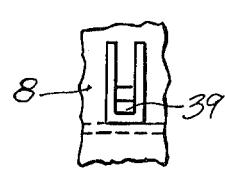
FIG. 4 is an elevational view showing details of the retention portion of the actuating mechanism illustrated in FIG. 3.

Referring now to FIG. 3, there is shown a modified catch-release system having provisions for minimizing accidental actuation of the syringe. The device includes a housing member 4 containing a liner 8 which is movable through the housing member 4 and which is biased by a spring 30. The liner 8 is made from a compatible plastic material and contains an upper elastomeric plug 13 and the dose of medication 14. An opening 36 is formed in the housing member 4 with one wall of the opening 36 providing a shoulder 36 which is engaged by a resilient tang 39 formed as an integral part of the liner 8. The construction of the tang 39 is shown in FIGS. 3 and 4. Thus, the tang 39 forms the catch which maintains the syringe in a cocked position. As an integral part of the housing member 4 on the exterior thereof, there is formed a release arm 32 having a projecting portion 34 aligned with the opening 36 and the tang 39. A safety ring or collar 40 is mounted on the housing member 4 and extends between the free end of the release arm 32 and the housing member 4 to prevent inward movement of the release arm 32. Thus, accidental actuation of the syringe is minimized. To actuate the syringe, the safety collar 40 is withdrawn from the housing member 4, and the release arm 32 is pressed inwardly causing the projecting portion 34 thereof to dislodge the tang 39 from engagement with the shoulder 37 whereupon the spring 30 drives the liner 8 through the housing member 4 and the injection is administered in the general manner previously described.

Referring now to FIG. 5, there is shown a somewhat modified embodiment of the system shown in FIGS. 3 and 4. The embodiment of FIG. 5 includes a housing 4 having two release arms 32 opposite a pair of openings 36. The liner 8 has a pair of resilient catch tangs 39 which hold the liner 8 in a cocked position within the housing 4. The safety ring 40 is removably mounted on the housing 4 and covers both openings 36 whereby accidental actuation of the device is minimized. Upon removal of the ring 40, the device is actuated by simultaneously depressing both release arms 32 to disengage the tangs 39. Thereafter, the device operates as previously described.

Referring now to FIG. 6, there is shown an additional embodiment of the syringe of this invention. This embodiment includes provisions for simplified assembly which will be more clearly pointed out herein. The syringe includes a housing denoted generally by the numeral 50, and which includes upper and lower cup-shaped halves 52 and 54, respectively. These two parts are joined along a joint 56 by means of adhesive, plastic welding, or the like.

The upper part 52 contains a compressed coil spring 58 which bears against and biases a guide and holder member 60 slidably mounted in the upper part 52. The holder member 60 contains an ampoule 62 containing a dose of medication 64. The ampoule 62 is closed by an elastomeric piston 66 slidable within the ampoule 62. On the exterior of the upper part 52 there is disposed a release arm 68 having an inwardly extending projection 70. The projection 70 is disposed opposite a thin-walled portion 72 of the upper housing part 52. A deflectable catch tang 74 is formed on the holder member 60 and engages a shoulder 76 formed on the inner wall of the upper housing part 52. Thus, the holder 60 and associated parts are held in the position shown in FIG. 6 against the bias of the spring 58 and ready for use. A safety member 78 is sandwiched between the release arm 68 and the housing wall so as to prevent accidental inward movement of the release arm 68. When the syringe is to be used, a tab 80 on the safety member 78 is pulled upwardly so as to bend or rupture a thin-walled part 82 of the safety member 78 whereupon the safety-member 78 will be removed from its blocking or safety position. Once the safety member 78 has been removed, the release arm 68 is pressed inwardly to rupture the thin wall 72 and push the catch tang 74 off of the shoulder 76.

The lower housing part 54 is formed with a pedestal 84 through which extends a needle passage 86. A needle 88 is positioned on the top of the pedestal 84 and extends into the needle passage 86. On the needle 88, there is mounted a column of crushable foam material 90. The foam column 90 is sandwiched between the top of the pedestal 84 and a ferrule 92 secured to the needle 88. A thin-walled web 94 closes the needle passage 86 and is pierced by the needle 88 when the device is actuated.

Once the catch tang 74 is released, the spring 58 drives the holder 60 and associated parts toward the pedestal 84. The needle 88 pierces the piston 66 and the latter is driven against the ferrule 92 with the result that the column 90 is crushed onto the pedestal 84 and the needle 88 is driven through the web 94 and into the flesh of the user. Once the ferrule 92 is driven to the top of the pedestal 84, movement of the needle 88 stops and the piston 66 is driven back into the ampoule 62 whereupon the medication 64 is pumped out through the needle 88 and into the flesh of the user. The ampoule 62 telescopes down over the pedestal 84 until the ampoule bottom wall 63 or the holder bottom wall 61 contacts the bottom inside surface 55 of the lower housing part 54.

In order to vary the dose of medication which may be administered by the device, one or more rings 96 may be mounted on the pedestal 84 to modify the extent of which the ampoule 62 can telescope over the pedestal 84. In this way, uniform ampoule sizes can be used in all syringes so as to contain a maximum medication dosage. In cases where less than a full dosage is required, one or more rings 96 may be properly positioned in the housing. For example, one ring could result in a 25% reduction of dosage, two rings in a 50% reduction of dosage, and so on. This system allows for uniformity of parts while increasing versatility of the syringe.

It will be understood that the embodiment of FIG. 6 can be sub-assembled in halves, which may be separately sterilized and can be finally assembled in a sterile environment by securing the joint 56.

It will further be appreciated that the device of this invention provides for a simple, inexpensive catch-release mechanism, adequate safety precautions preventing premature or accidental actuation, and a simple needle positioning device embodying the crushable foam mass. By providing means for varying the dosage capabilities of the device without departing from its automatic operation, versatility is increased at minimal expense. It will be appreciated that the rings 96 are merely a preferred mode for achieving dosage variation and that alternative approaches could be taken, as for example, by varying the height of the pedestal 84.

As can be appreciated from FIG. 1, the medication-containing liner 8 may be entirely dispensed with if the intended medication is compatible with the body material 4. It should also be noted that in the versions shown in FIGS. 3 and 6, the crushable foam means could be substituted with a ferrule-type holder affixed to lower plunger 12 or 66.

Since many changes and variations of the disclosed embodiments of the invention may be made without departing from the inventive concept, it is not intended to limit the invention otherwise than as required by the appended claims.

What is claimed is:
1. An automatic hypodermic syringe comprising:
 (a) a housing;
 (b) means containing an injectable medication within said housing;
 (c) a hypodermic needle disposed within said housing;
 (d) means for driving said hypodermic needle from a retracted position within said housing to an injecting position wherein a portion of said needle protrudes from said housing; and
 (e) foam means in said housing for engaging said needle to hold said needle properly in said retracted position, said foam means being readily crushable so as to allow said needle to be driven to said injecting position.

2. An automatic hypodermic syringe comprising;
 (a) a housing;
 (b) first means containing a dose of medication disposed within said housing;
 (c) a hypodermic needle disposed in said housing in a retracted position, and movable to an injecting position wherein said needle projects from said housing;
 (d) movable means in said housing for moving said medication toward said needle whereby said needle will puncture said first means to penetrate said medication, and whereby said needle will be moved to said injecting position;
 (e) spring means in said housing for providing a driving force needed to move said movable means toward said needle;
 (f) catch means for retaining said movable means in a retracted position wherein said medication is disposed away from said needle; and
 (g) release means formed as an integral and unitary part of said housing, said release means being operable to release said catch means whereby said movable means is driven by said spring means from said retracted position.

3. The syringe of claim 2, further comprising safety means mounted on said housing for engaging said release means to prevent operation of said release means.

4. The syringe of claim 2, wherein said catch means comprises a resilient tang formed as an integral part of said movable means, and a shoulder in said housing which is engaged by said tang to prevent movement of said movable means.

5. An automatic hypodermic syringe comprising:
 (a) a first cup-shaped member formed as a one-piece unit having an integral closed end and an opposite open end;
 (b) means forming a medication holder in said first cup-shaped member and movable therein toward said open end of said first cup-shaped member;
 (c) catch means in said first cup-shaped member for releasably retaining said holder in a retracted position;
 (d) spring means sandwiched between said medication holder and said closed end of said first cup-shaped member for biasing said medication holder toward said open end of said first cup-shaped member;

(e) a second cup-shaped member formed as a one-piece unit having an integral closed end and an opposite open end;

(f) a hypodermic needle disposed in said second cup-shaped member;

(g) means positioning said hypodermic needle in said second cup-shaped member;

(h) the open ends of said first and second cup-shaped members being disposed in face-to-face contact and joined together to form a sealed closed housing for said syringe; and (i) release means on said housing for selectively engaging said catch means to disable the latter from retaining said holder in said retracted position.

6. The syringe of claim 5, further comprising safety means on said housing for preventing unintentional actuation of said release means.

7. An automatic hypodermic syringe comprising:

(a) a housing having a hollow interior;

(b) a pedestal on one end wall of the interior of said housing, said pedestal extending axially into the interior of said housing, and said pedestal having an axial needle passage therein;

(c) means sealing said needle passage at said one end wall of said housing;

(d) a hypodermic needle disposed in the interior of said housing and extending into said needle passage; (e) ampoule means containing an injectable medication in said housing, said ampoule means having a fixed end wall remote from said pedestal and a movable end wall proximate said pedestal;

(f) spring means for driving said ampoule means in said housing toward said pedestal and into telescoping relationship over the latter whereby said needle will puncture said movable end wall of said ampoule and said needle will be driven to an injecting position wherein said needle protrudes from said housing, said pedestal being operable to engage said movable end wall of said ampoule means and drive said movable end wall into said ampoule means as the latter telescopes over said ampoule means to cause the medication to be pumped through said needle; and (g) stop means in said housing adjacent to said pedestal for engaging an end wall of said ampoule means to prevent said ampoule means from fully telescoping over said pedestal whereby only a fraction of a maximum dose of medication in said ampoule means will be pumped through said needle.

8. The syringe of claim 7, wherein said stop means is one or more rings disposed in said housing surrounding said pedestal adjacent to said one end wall of said housing.

* * * * *